United States Patent [19]

Kim

[11] Patent Number: 5,743,908
[45] Date of Patent: Apr. 28, 1998

[54] BI-DIRECTIONAL BI-POSITIONAL UNIVERSAL DYNAMIC COMPRESSION DEVICE

[76] Inventor: Andrew C. Kim, 30213 Del Rey Rd., Temecula, Calif. 92591

[21] Appl. No.: 835,612

[22] Filed: Apr. 9, 1997

Related U.S. Application Data

[63] Continuation-in-part of Ser. No. 674,784, Jul. 3, 1996, which is a continuation-in-part of Ser. No. 618,366, Mar. 19, 1996, Pat. No. 5,658,288.

[51] Int. Cl.⁶ ............................................. A61B 17/72
[52] U.S. Cl. ............................................ 606/64; 606/73
[58] Field of Search .................... 606/60, 62, 63, 606/64, 65, 72, 73, 66, 67, 68, 69, 70, 71, 105

[56] References Cited

U.S. PATENT DOCUMENTS

| | | | |
|---|---|---|---|
| 2,821,979 | 2/1958 | Cameron | 128/92 |
| 4,622,959 | 11/1986 | Marcus | 128/92 |
| 4,875,475 | 10/1989 | Comte et al. | 128/924 |
| 4,911,153 | 3/1990 | Border | 606/98 |
| 5,281,224 | 1/1994 | Faccioli et al. | 606/62 |
| 5,458,600 | 10/1995 | Stapert et al. | 606/63 |
| 5,480,402 | 1/1996 | Kim | 606/64 |

FOREIGN PATENT DOCUMENTS

| | | |
|---|---|---|
| 384 359 B | 10/1987 | Austria . |
| 19 30 354 | 5/1978 | Germany . |

*Primary Examiner*—Michael Buiz
*Assistant Examiner*—David O. Reip
*Attorney, Agent, or Firm*—Baker, Maxham, Jester & Meador

[57] ABSTRACT

A compression interlocking system for stabilizing long bone fractures, comprises an elongated intramedullary rod having a proximal end, a distal end and a longitudinal axis, the rod adapted for extending within a bore generally parallel to a longitudinal axis of a long bone from a proximal end of the bone to beyond a fracture of the bone, a first member for fixing the proximal end of the rod to a first portion of a bone having a fracture, a second member for fixing the distal end of the rod to a second portion of the bone having the fracture, and a cam associated with at least one of the first and second members for moving the first portion of the bone and the second portion of the bone toward one another for closing and applying compression to the fracture.

18 Claims, 6 Drawing Sheets

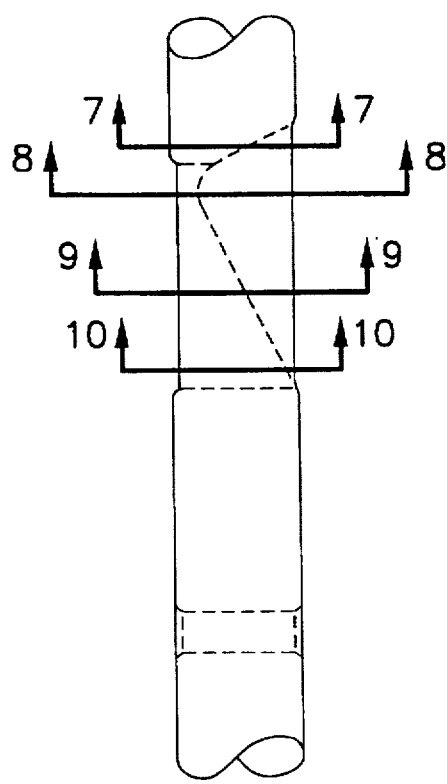
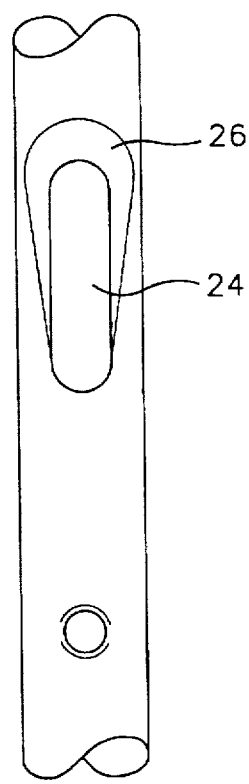
FIG. 5  FIG. 6
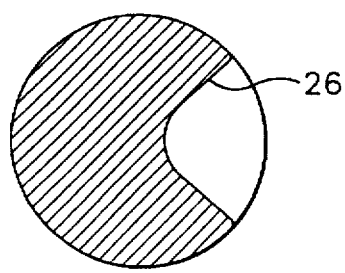
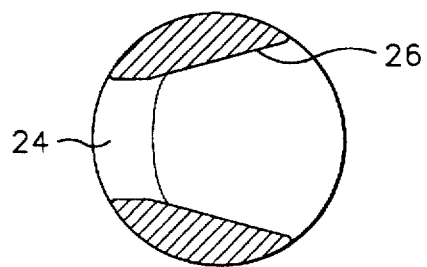
FIG. 7  FIG. 8
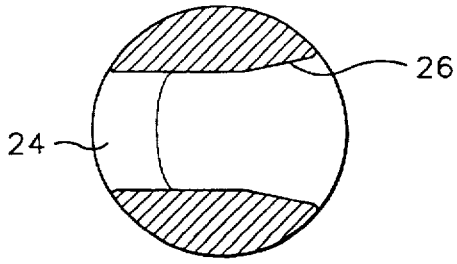
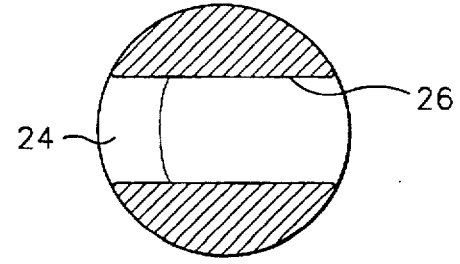
FIG. 9  FIG. 10

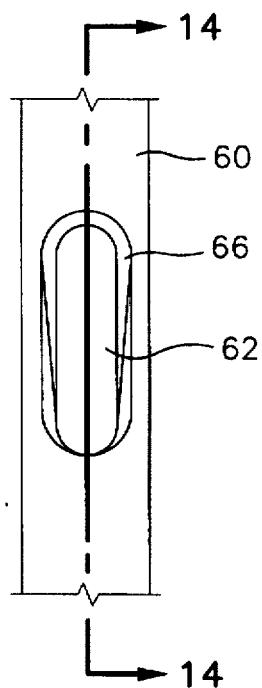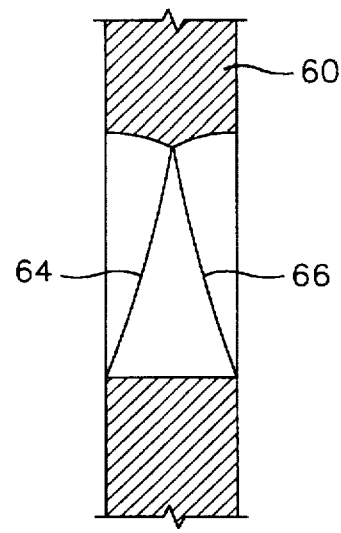
FIG. 13
FIG. 14
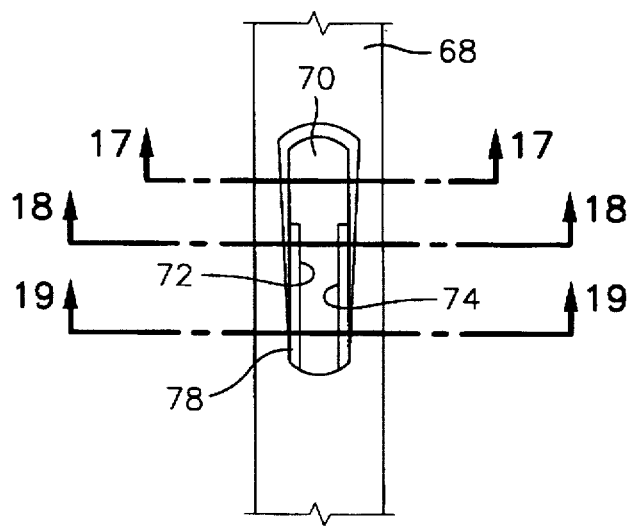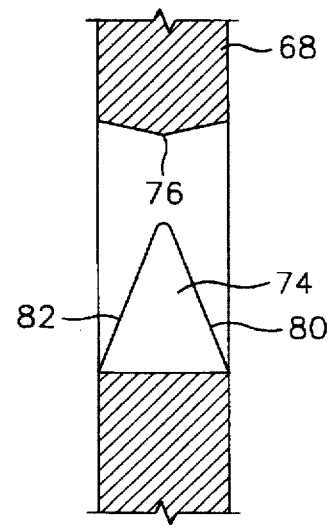
FIG. 15
FIG. 16

BI-DIRECTIONAL BI-POSITIONAL UNIVERSAL DYNAMIC COMPRESSION DEVICE

REFERENCE TO RELATED APPLICATION

The present invention is a continuation-in-part of pending Ser. No. 08/674,784, filed on Jul. 3, 1996, which is a continuation-in-part of Ser. No. 08/618,366, filed Mar. 19, 1996, now U.S. Pat. No. 5,568,288.

BACKGROUND OF THE INVENTION

The present invention relates to medical devices and pertains particularly to an improved rod fixation and compression system for fractures in long bones.

Fractures in long bones in the human body can properly heal only if the two portions of the fractured bones are properly positioned and fixed relative to each other. Such fractures are frequently assisted in their mending by utilizing either an external or internal splint. Internal splints are preferred for most fractures and consist of an elongated intramedullary rod or nail inserted in a bore extending along the axis of the bone and secured by screws to tie the two parts of the fractured bone together until healing can occur. A major difficulty with prior art devices in the case of humerus is that non-union or delayed union frequently occurs. I have found that part of the reason is that the applied force is tensile force rather than compression required to force the two parts of the fractured bone together to enable mending.

In my prior patent, U.S. Pat. No. 5,480,402, entitled "Shoulder Compression Interlocking System", I disclosed an improved rod and interlocking system which improved the stabilization of bone fractures. However, that structure was unable to apply the necessary compressive forces discovered to be necessary.

In fracture healing, there are two basic requirements: osteoconduction and osteoinduction. Osteoconduction is a physical, mechanical requirement. Contact or continuity of bone ends is important for fracture healing. Osteoinduction is the consideration of biological biomechanical induction of bone healing and bone formation. Blood circulation, soft tissue preservation, Wolf's law are important considerations for osteoinduction.

Nonsurgical treatment with cast application stresses osteoinduction aspect in fracture healing. Surgical fixation, such as plate fixation stresses more of the osteoconduction aspect. In this method, a small gap in the fracture fixation can be very harmful with danger of nonunion developing. Successful healing of the callus tissue is affected by the stress it received (Perren). Stress is a function of the following factors:

$$\text{Stress } \alpha \frac{\Delta l}{l}$$

Δl=in the gap
l=width of the gap

Therefore, a small gap in internally fixed fracture imposes greater danger of developing nonunion than a nonoperative fracture with a larger gap. Under such circumstances, there is already less reliance on osteoinduction and the benefit of osteoconduction is compromised by micromotion significant in proportion to the size of the gap.

Intramedullary rod fixation without interlocking provides internal splint effect. It gives closer reduction to provide better anatomical alignment and osteoconduction effect. Weight bearing allows compression of fracture site narrowing gaps. The rod still allows transfer of Wolf's stress and osteoinduction. However, an intramedullary rod system does not provide torsional stability. Therefore interlocking intramedullary fixation system was devised to compensate for torsional stability or to prevent excessive shortening when a comminuted fracture did not provide cortical stability.

Interlocking intramedullary rod systems are currently widely used. As a result, the interlocking system, though it may provide rotational stability, usually creates a fixed gap at the fracture site. The gap bypasses the stress from the bone to the implant sometimes causing implant failure such as screw or rod breakage. Delayed union is the frequent result.

Interlocking rod fixation does not completely eliminate micro motion due to an oscillating or windshield wiper effect. To eliminate the windshield wiper effect, some manufacturers made two plane interlocking in the distal tibia. The two plane interlocking requires more soft tissue disturbance and increases risks of injury.

A more ideal system would be an interlocking rod with minimal micromotion but with compression or elimination of any gap. The benefits of the present invention in comparison can be summarized as follows:

1) Narrows the fracture gap to the point of contact providing osteoconduction.
2) Eliminates micromotion.
3) Provides dynamic compression at the fracture site, and therefore, osteoinduction through Wolf's stress.
4) Shares the stress through the fractured long bone between the bone and the implant rather than having the implant take up the entire stress. As a result, implant failure such as rod or screw breakage will be minimized.
5) Reduces motion at the distal interlocking (windshield wiper motion) by internal locking of the rod with this newly designed compression screw. Therefore, with one plane approach it achieves the benefit of two plane stability.
6) Provides compression from either or both ends of the rod.

The aforementioned parent application solved many of the above problems by providing an improved intramedullary system for providing compression to the fracture site to help bring about faster healing with less implant failure. However, that system suffers from the inability to apply it universally, i.e. equally to opposite sides, such as the right or left side.

In the first mentioned parent application above, I disclose a bi-directional universal compression device that enables one to insert the compression lag screw from one or more different sides, such as adjacent sides or opposite sides. This is particularly advantageous where the rod is curved and enables a single rod to service in many applications. Suitable modifications to the rod could be made either by providing an additional hole with a cam, or by providing an additional cam in a common hole, i.e. engageable from either end.

The advantage of using a single cam for each of two or more holes is that the slope of the cam can be greater with a single cam from one side of the hole. This greater slope could have the effect of reducing the stress on the bone into which the rod is installed. It could also enable the provision of a greater length to the slot and cam to accommodate larger displacement of the bone sections. It also enables the provision of the cammed compression slot at any number of different angles about and positioned along the length of the rod.

These devices have been shown to be constructed with the cam on the distal end of the rod and only on one side of the fracture. However, the inventor has discovered that the cam can be on either end or the rod or on either or both sides of the fracture. In some cases it has been found to be desirable to have the cam on the proximal end (head end) of the rod. In other cases it is desirable to have a cam on either side of the fracture. This can increase the range of compression as well as improve accessibility to the compression means.

It is therefore desirable to have a long bone fixation device that is simple and universally applicable to both sides of the bone and either or both sides of the fracture.

There is a need for an improved universal intramedullary system for providing a greater range of compression to the fracture site to help bring about faster healing with less implant failure.

SUMMARY AND OBJECTS OF THE INVENTION

It is therefore a primary object of the present invention to provide a more universal and effective long bone fixation device.

In accordance with a primary aspect of the present invention, a compression interlocking system for stabilizing long bone fractures, comprises elongated intramedullary rod means having a proximal end, a distal end and a longitudinal axis, said rod means adapted for extending within a bore generally parallel to a longitudinal axis of a long bone from a proximal end of the bone to beyond a fracture of the bone, first means for fixing said proximal end to a first portion of a bone having a fracture, second means for fixing said distal end to a second portion of the bone having the fracture, and compression means associated with one of said first and second means for fixing and comprising cam means accessible from at least one side of said rod and a lag screw having shoulder means for engaging said cam means for moving one of said first and second portion of the bone toward the other of said first and second portion of the bone for applying compression to the fracture.

BRIEF DESCRIPTION OF THE DRAWINGS

The objects, advantages and features of this invention will be more readily appreciated from the following detailed description, when read in conjunction with the accompanying drawing, in which:

FIG. 5 is an enlarged partial side elevation view of the cam area of the rod;

FIG. 6 is an enlarged partial front elevation view of the cam area of the rod;

FIG. 7 is a section view taken generally along line 7—7 of FIG. 5;

FIG. 8 is a section view taken generally along line 8—8 of FIG. 5;

FIG. 9 is a section view taken generally along line 9—9 of FIG. 5;

FIG. 10 is a section view taken generally along line 10—10 of FIG. 5.

FIG. 13 is a front elevation view showing an alternate embodiment with a bi-directional cam and slot arrangement;

FIG. 14 is a section view taken generally on line 14—14 of FIG. 13;

FIG. 15 is a view like FIG. 13 of a further embodiment of the invention;

FIG. 16 is a view like FIG. 14 of the embodiment of FIG. 15;

DETAILED DESCRIPTION OF PREFERRED EMBODIMENTS

Figure 1:
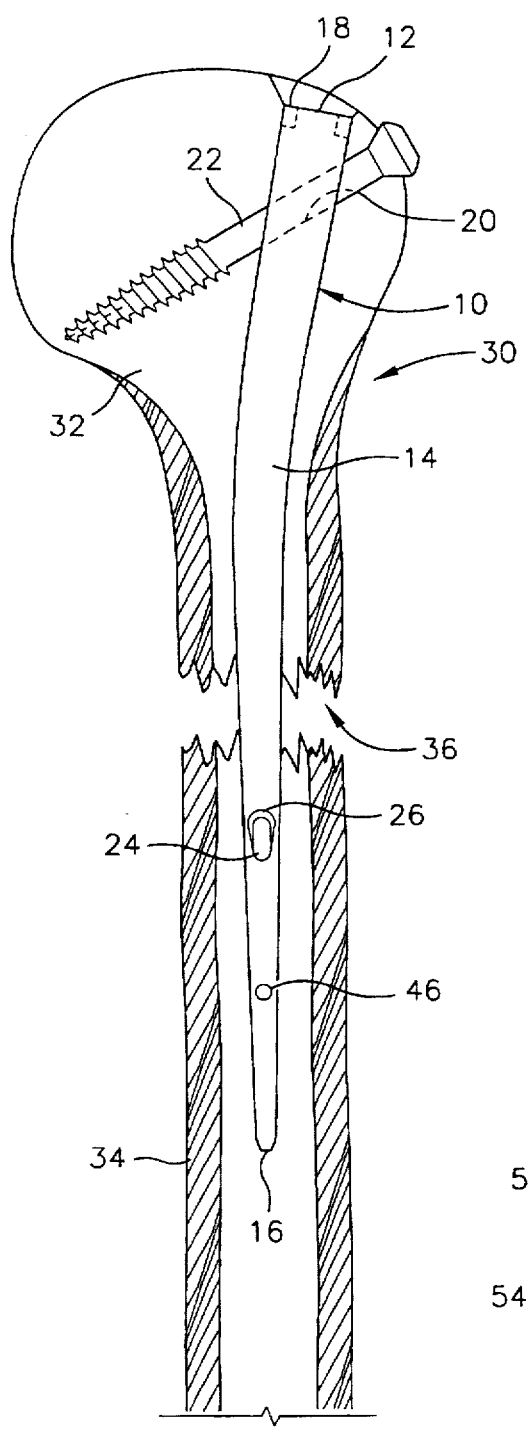
FIG. 1 is a front elevation view of an exemplary preferred embodiment of the invention shown in position for use.

The present invention is directed to an improved intramedullary rod fixation system for long bones for fixation of bones that have been fractured. Referring specifically to FIG. 1 of the drawings there is illustrated a front elevation view in section of a bone having an exemplary embodiment of the rod designated generally by the numeral 10, in accordance with the invention positioned therein. The rod (sometimes called pin or nail in the art) comprises an elongated unitary or integral hollow body having a head or proximal end 12 an elongated intermediate body portion 14 and a distal tip 16. The head end 12 may be formed by a suitable threaded bore and is provided with alignment lugs 18. These lugs are used in conjunction with a guide fixture for alignment for drilling and insertion of lag screws as is known in the art. The rod 10 is provided with one or more transverse screw receiving bores 20 near the proximal end for receipt of fixation lag screws 22. It may be similarly provided with one or more similar bores near the distal tip so as to be positioned beyond the fracture which it is to fix.

An oblong transverse bore 24 is formed in an intermediate position of the shank of the rod 14 at a position to be beyond a fracture in a bone in which the rod is mounted. Surrounding the bore or hole 24 is a cam 26 which cooperates with a shoulder on a specially constructed lag screw 28 for applying compression to a fracture between two portions of a fractured bone. The cam 26 is formed by a sloping surface surrounding the hold or bore 24. The rod, as illustrated in FIG. 1 is inserted into a longitudinally extending bore formed along the center axis of a long bone designated generally by the numeral 30. The bone, as illustrated, has an upper portion 32 and a lower portion 34 which has been fractured from the upper portion along a fracture 36. In the illustrated embodiment the rod 14 has been inserted along the bone in a conventional fashion. The present invention is designed to be utilized in any long bone of the body, such as the humerus, femur, tibia and other bones. The rod preferably has a cannula or elongated longitudinal bore to enable the use of a guide wire (not shown) in a conventional fashion.

Figures 2, 3, 4:
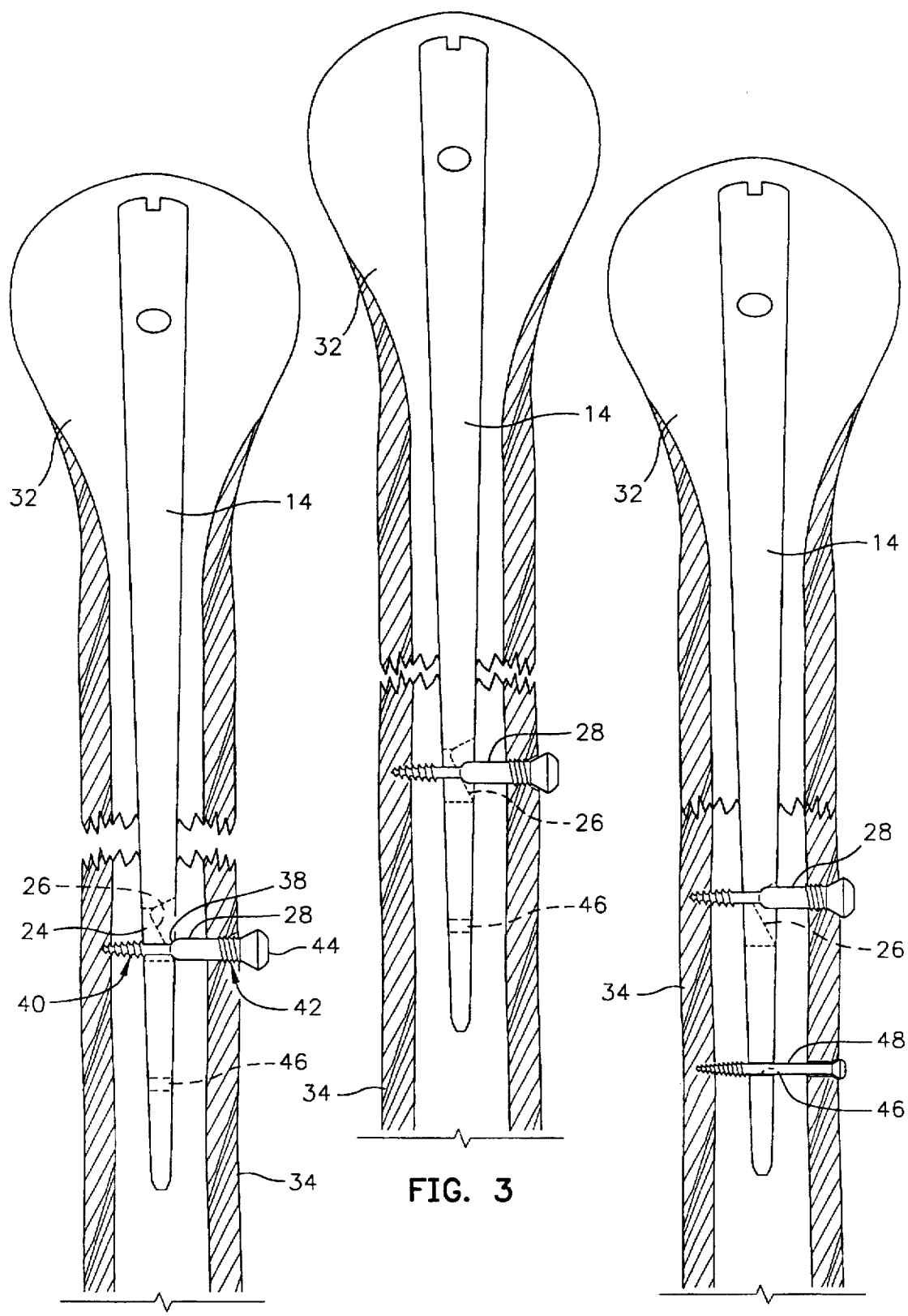
FIG. 2 is a side elevation view of the embodiment of FIG. 1 showing the invention in a first stage of applying compression to a fracture.
FIG. 3 is a view like FIG. 2 showing the invention in a second stage of applying compression to a fracture.
FIG. 4 is a view like FIG. 2 showing the invention in a final stage of applying compression to a fracture.

Referring to FIG. 2 of the drawing a side elevation view in section of the embodiment of FIG. 1 showing the compression mechanism of the present invention is illustrated. As illustrated, the bore 24 extends across the rod and is oblong or has a somewhat oval configuration defining a somewhat slot like structure extending along the longitudinal axis of the rod 14. Surrounding the bore is a sloping cam track 26 which forms a wedge-like cam sloping inward in the longitudinally upward direction, or toward the head of the rod or pin. This track cooperates with a shoulder 38 on the stepped diameter lag screw 28 between a smaller diameter portion 40 at the distal end and a larger diameter portion 42 near the head 44 of the lag screw. The forward or distal end of the lag screw 28 is formed with self-tapping threads to aid in threading the screw into the bone portion 34. The lag screw is also formed with self-tapping threads on the larger portion 42 at the head and preferably with a non-threaded portion adjacent the shoulder on the head side. The head 44 is preferably formed with a hex socket for engagement with an Allan wrench.

In operation, once the rod 14 has been inserted into a bone 30, as shown in FIG. 1, a typical guide instrument is utilized to align a suitable drill with bores at the upper end of the rod, such as bore 20 to enable the drilling of holes for insertion of lag screw 22. Additional screws may be utilized in the arrangement, shown for example in my prior patent, identified above. Once the rod is anchored in the upper portion 32 of the bone 30 the lower bone is properly positioned and properly oriented. The bone portion intersecting to locate and drill a hole in the bone portion intersecting the bore 24, as shown in FIG. 2. Preferably the hole through the bone will intercept the oblong bore 24 at its lower most end so that when screw 28 is inserted, ample room for biasing and movement of the bone and screw upward to establish compression in the fracture will be provided. As will be appreciated, the screw 28 having a step diameter, a first drill for portion 40 will be drilled through the bone in alignment with the lower most end of bore 24. Thereafter, a larger hole will be made up to the edge of the rod 14. A preferred method is the utilization of a cannulated or hollow second diameter bore drill that fits over the first drill utilizing the first drill as a guide to maintain precise alignment.

Once the hole is made into the bone, the screw 28 is inserted through hole 24 and threaded into the far side of the bone. As the screw threads into the bone, the shoulder 38 of screw 28 engages and biases against cam surface 26. As the screw 28 moves further inward, it rides upward on the slope 26 carrying the bone portion 34 there along to further move the bones closer together in the area of the fracture 34, as shown in FIG. 3. The screw 28 is threaded in until the lower bone portion moves into engagement with the upper portion 14 and a suitable compression is established. In the ideal position, a suitable compression is reached as the screw approaches or nears the bottom of the slope of the cam 26, as shown in FIG. 4.

The rod 14 may have a curved configuration, as illustrated, or may have a straight configuration depending on its application. The dimensions of the rod including length, diameter, number and position of holes may also vary, depending on the requirements.

Figure 11:
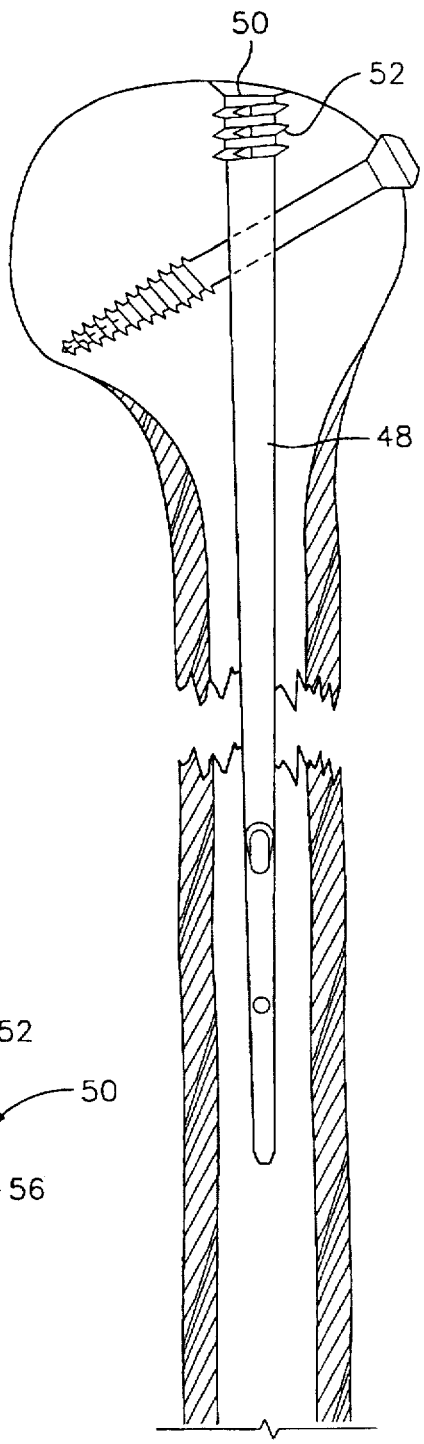
FIG. 11 is a view like FIG. 1 of an alternate embodiment of the invention.

Referring to FIG. 11, further embodiment is illustrated showing a straight rod 48 and utilizing a fixation thread 52 at the top or head 50, as illustrated. The straight rod can be rotated to fix it in the bone by threads 52, which are preferably self-tapping. Additional bores may be provided in the rod in any number of positions and angles, such as disclosed in my prior patent. The additional bores may be positioned to receive conventional lag screws to more securely fix the bone portions to the rod.

Figure 12:
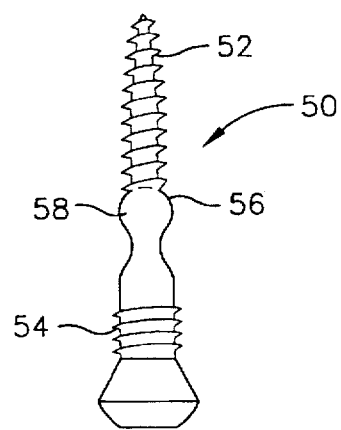
FIG. 12 is a side elevation view of an alternate embodiment of a lag screw.

Referring to FIG. 12, an alternate embodiment of a compression lag screw designated generally by the numeral 50 is illustrated. The screw has a reduced diameter threaded forward portion 52 and an enlarged threaded rear portion 54. A bearing shoulder 56 is formed by a spherical portion intermediate the two different diameter portions of the lag screw with the larger diameter portion down to provide a greater spherical surface. This construction may be preferred in many applications.

Referring to FIGS. 13 and 14, a rod 60 is formed with a double cam elongated through slot 62 having opposing cam surfaces 64 and 66. The cam surfaces 64 and 66 are directly opposed to one another at opposite ends of the bore 62. The cam surfaces, as will be appreciated, have a depth of only ½ of the diameter of the rod 60 with a length equal to the height or length of the slot 62. With this arrangement, a lag screw such as that illustrated at 28 in FIGS. 2–4, or that in FIG. 12 may be inserted from either side of the rod 60. Thus, the rod becomes universal in the sense that it can be utilized for the left or right side, for example. The depth of the cam, however, may be on the order of about ½ that of a single cam bore, as in the previous embodiments. This results in a shallower slope cam surface, thus resulting in lower (lesser) forces on the bone structure to cam the bone structures together.

Referring to FIGS. 15 and 16, an alternate embodiment is illustrated wherein a rod 68 is formed with an oblong through slot 70 having a pair of opposed cams formed by triangular cam structures 72 and 74. The cam structure 72 and 74 terminates short of the top wall 76 of the bore 70, thereby leaving an opening through which the lag screw or bolt may extend, as will be subsequently explained. This cam structure provides a steeper slope than that of FIGS. 13 and 14, thereby providing greater compression on the bone structure. This structure may also provide substantially the same distance of movement of the bone structure bringing the two bone portions together.

The cam structure 72 forms two cam surfaces, only one of which, 78, is illustrated. The cam structure 74 similarly forms two cam surfaces, 80 and 82 as shown in FIG. 16, which may be engaged by a lag screw from opposite sides of the rod.

Figure 17:
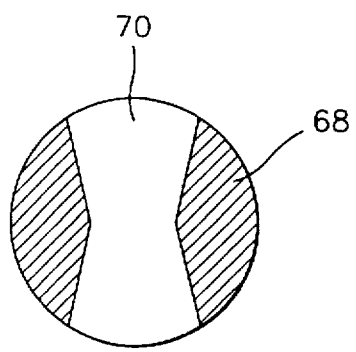
FIG. 17 is a section view taken on line 17—17 of FIG. 15.
Figure 18:
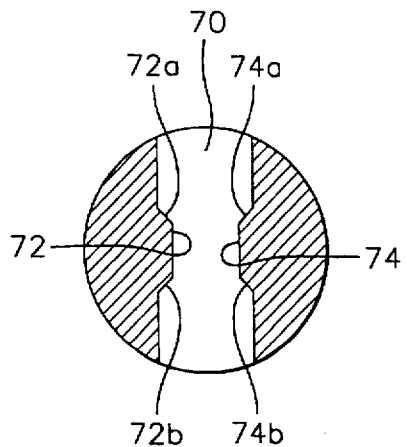
FIG. 18 is a section view taken on line 18—18 of FIG. 15.
Figure 19:
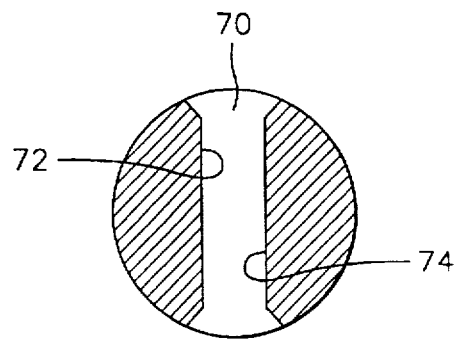
FIG. 19 is a view taken on line 19—19 of FIG. 15.

Referring to FIGS. 17, 18 and 19, cross-sectional areas of the through bore with the cam structure are illustrated. As is illustrated in FIGS. 17, the upper portion of the bore 70 above the cam structure provides an opening for substantial passage of the lag screw, as will be described. It will also be appreciated, as shown in FIG. 17, that the slot opens outward at both sides to accommodate minor deviations of the direction of the screw at insertion. Thus, minor deviations of the rod about its axis are accommodated allowing the screw to be inserted into the cross slot.

Referring to FIG. 18, a top portion of the cam surfaces is illustrated, showing the cam and its projection inward into the cross slot. The camming surfaces 72a and 72b and 74a and 74b are shown angled toward the sidewalls of the slot. However, they may extend straight in toward the wall (i.e. at 90°).

FIG. 19 illustrates a cross-section of a lower portion of the slot and cam combination. It would have the stone slope and angle to the walls.

Figure 20:
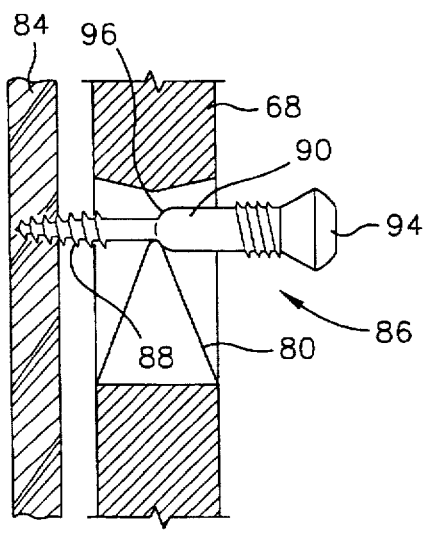
FIG. 20 is a side elevation view in section showing a rod positioned in a bone structure with a lag screw in a position of partial insertion.

Referring to FIG. 20, a cross-sectional view of a rod 68 inserted into a bone, a portion of which, 84, is illustrated. A lag screw designated generally at 86, has a distal reduced diameter threaded portion 88 and a proximal larger diameter portion 90 having a threaded section 92 adjacent a head 94. A shoulder 96 of a semispherical configuration forms a transition between the larger diameter portion 90 and the smaller diameter portion 88. The shoulder 96 engages the laterally adjacent cam surfaces 78 and 80 and cams the bone section 84 upward relative to the rod 68. This closes and applies a compression to the fracture, as previously described with respect to other embodiments.

As shown in FIG. 20, the screw 90 has reached substantially the end of the cam surfaces with a little further camming distance to go.

Figure 21:
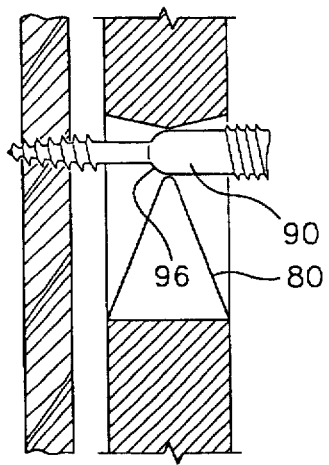
FIG. 21 is a view like FIG. 20 showing the lag screw in a further advanced position of insertion.

Referring to FIG. 21, the screw 86 has reached the end of the cam surface 80 thereby reaching the end of movement of the bone section relative to the rod 68.

Figure 22:
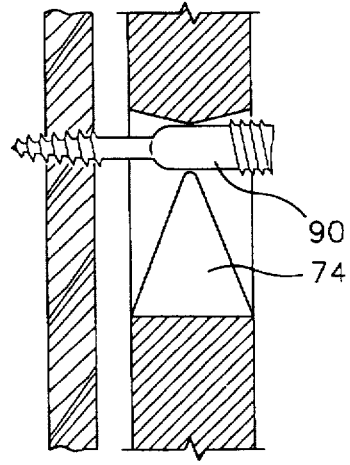
FIG. 22 is a view like FIG. 21 showing the lag screw in the fully inserted position.

Referring to FIG. 22, the lag screw portion 90 has extended beyond the tip of the cam 74 and partially across the bore, thereby locking the bone and rod together. Thus, it can be seen that there are described embodiments wherein a lag screw can be inserted from different angles about the axis of the rod, thereby providing a universal compression assembly.

Figure 23:
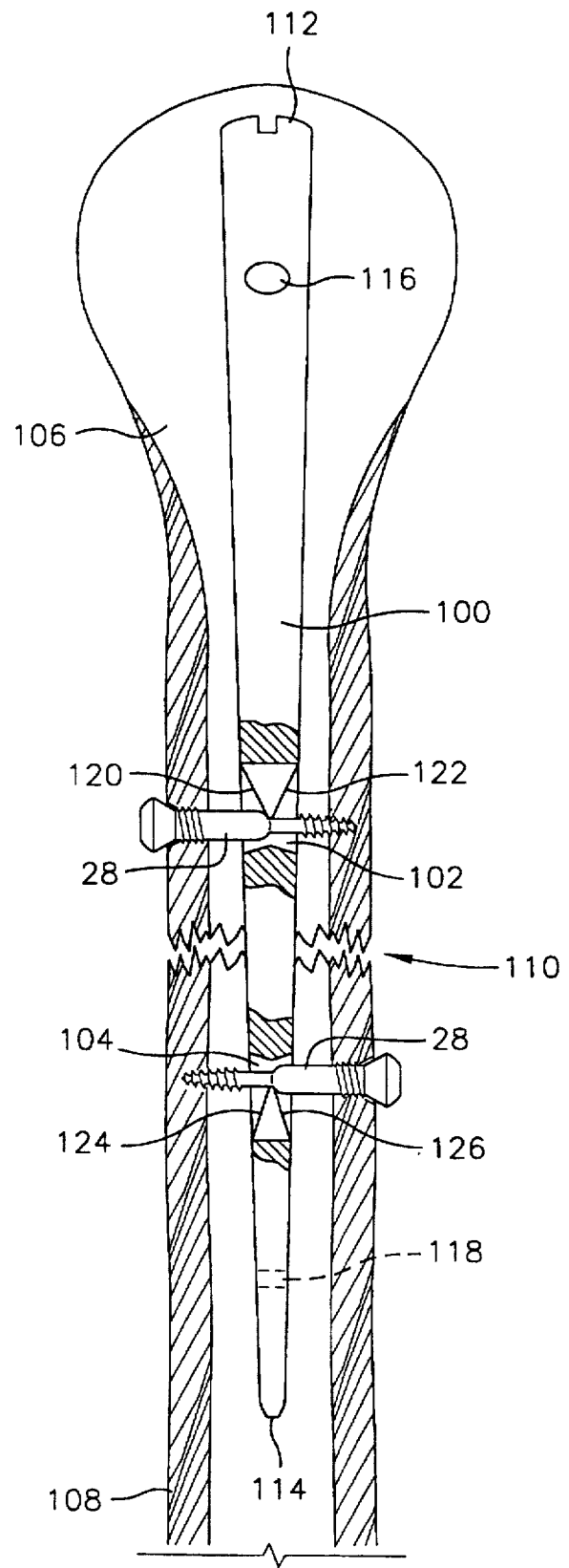
FIG. 23 is a view like FIG. 3 showing an alternate embodiment of the invention shown in position for use.

Referring to FIG. 23, an alternate embodiment is illustrated wherein a rod 100 is shown formed with two double cam slots 102 and 104. The rod is positioned in a fractured bone so that one cam slot is in one of two bone segments 106 and 108 on either side of a bone fracture 110. The rod has a head or proximal end 112 with suitable fixation means such as a bore 114 and a tip end or distal end 116 with a fixation bore 118.

As illustrated, the compression means 102 and 104 for the rod can be on either side or both sides of the fracture. For example, the rod can have either multiple double cam slots as illustrated or it can have one double cam slot and position the cam slot on either side of the fracture. That is the cam slot can be on or toward the head end of the rod from the fracture or toward or on the tip side or end of the rod from the fracture. The cam or cams in either case will point or slope toward the fracture.

As illustrated in FIG. 23, a cam slot 102 is formed with opposing cam surfaces 120 and 122 which are positioned toward the head end 112 of the rod and slope or point toward the fracture 110. Similarly, cam slot 104 is formed with opposing cam surfaces 124 and 126 positioned toward the tip end 114 of the rod and slope toward the fracture 110. Either cam unit can be effective to pull the bone fragments together at the fracture. A lag screw 28 as in prior embodiments may be used in one or both of the cam units or structures to apply the necessary compression to the fracture. The lag screw can also enter the cam slot from either end or the cam slot or side of the rod. The provision of two double cam units as illustrated enables greater movement of the bone fragments and enables application of greater compression to the fracture.

While I have illustrated and described my invention by means of specific embodiments, it is to be understood that numerous changes and modifications may be made therein without departing from the spirit and the scope of the invention as defined in the appended claims.

I claim:

1. A compression interlocking system for stabilizing long bone fractures, comprising:

elongated intramedullary rod means having a proximal end, a distal end and a longitudinal axis, said rod means adapted for extending within a bore generally parallel to a longitudinal axis of a long bone from a proximal end of the bone to beyond a fracture of the bone;

first means for fixing said proximal end to a first portion of a bone having a fracture;

second means for fixing said distal end to a second portion of the bone having the fracture; and compression means associated with one of said first and second means for fixing and comprising cam means accessible from at least one side of said rod and a lag screw having shoulder means for engaging said cam means for moving one of said first and second portion of the bone toward the other of said first and second portion of the bone for applying compression to the fracture.

2. A system according to claim 1 wherein said compression means comprises cam means on opposite sides of said rod and said lag screw having shoulder means adapted for selectively engaging said cam means from either side.

3. A system according to claim 1 wherein said cam means comprises an elongated transverse bore in said rod, a sloping surface surrounding said elongated bore in said rod, and said lag screw adapted for extending through said bore and anchoring in one of said first and said second portion of said bone.

4. A system according to claim 3 wherein said cam means comprises a sloping surface surrounding said bore at each end of said bore.

5. A system according to claim 4 wherein said cam means is disposed toward said distal end of said rod from a center thereof and said sloping surface slopes inward toward said center from said distal end.

6. A system according to claim 4 wherein said cam means is disposed toward said proximal end of said rod from a center thereof and said sloping surface slopes inward toward said center from said proximal end.

7. A system according to claim 1 wherein said cam means comprises a transverse bore in said rod, said bore having an elongated diameter longitudinally of said rod, a sloping surface surrounding said elongated bore, and said lag screw adapted for extending through said bore and having rounded shoulder means for engaging said cam and anchoring to said bone portion.

8. A system according to claim 7 wherein said cam means is disposed toward said distal end of said rod from a center thereof and said sloping surface slopes inward toward said center from said distal end.

9. A system according to claim 7 wherein said cam means is disposed toward said proximal end of said rod from a center thereof and said sloping surface slopes inward toward said center from said proximal end.

10. A system according to claim 9 wherein said cam means comprises a sloping surface surrounding said bore at each end of said bore.

11. A system according to claim 8 wherein said cam means comprises a sloping surface surrounding said bore at each end of said bore.

12. A system according to claim 1 wherein said cam means comprises first cam means comprising a sloping surface disposed toward said distal end of said rod from a center thereof and said sloping surface slopes inward toward said center from said distal end, and second cam means comprising a sloping surface disposed toward said proximal end of said rod from a center thereof and said sloping surface slopes inward toward said center from said proximal end.

13. A compression interlocking system for stabilizing long bone fractures, comprising:

elongated intramedullary rod means having a proximal end, a distal end and a longitudinal axis, said rod means adapted for extending within a bore generally parallel to a longitudinal axis of a long bone from a proximal end of the bone to beyond a fracture of the bone;

fixing means for fixing one of said proximal end and said distal end to a first portion of a bone having a fracture;

a transverse bore in the rod means for positioning in a second portion of the bone at a position beyond the fracture from said one of said proximal end and said distal end, said transverse bore having a predetermined diameter and a configuration enabling a lag screw to move longitudinally of the rod when viewing in elevation view of the rod means;

cam means on said rod adjacent said bore for engaging and camming a lag screw along from either side of said axis of said rod means so that said lag screw may be moved along said axis relative to said rod; and a stepped diameter lag screw for extending across said second portion and through said transverse bore, said lag screw having a stepped diameter with a forward end having a diameter less than said predetermined diameter and a rear end greater than said predetermined diameter, and a shoulder between said diameters for engaging said cam means on said rod.

14. A system according to claim 13 wherein said bore has an elongated diameter disposed longitudinally of said rod, and said cam means comprises an elongated sloping surface surrounding each end of said elongated bore, said lag screw having rounded shoulder means for engaging said cam.

15. A system according to claim 14 wherein said proximal fixing means for fixing said proximal end comprises self-tapping threads on said proximal end.

16. A system according to claim 14 wherein said cam means cam means is disposed toward said distal end of said rod from a center thereof and said sloping surface slopes inward toward said center from said distal end.

17. A system according to claim 14 wherein said cam means is disposed toward said proximal end of said rod from a center thereof and said sloping surface slopes inward toward said center from said proximal end.

18. A system according to claim 14 wherein said cam means comprises first cam means comprising a sloping surface disposed toward said distal end of said rod from a center thereof and said sloping surface slopes inward toward said center from said distal end, and second cam means comprising a sloping surface disposed toward said proximal end of said rod from a center thereof and said sloping surface slopes inward toward said center from said proximal end.

* * * * *